United States Patent
Suzuki et al.

Patent Number: 5,252,437
Date of Patent: Oct. 12, 1993

[54] PHOTOCHROMIC MATERIALS HAVING A THIN PHOTOCHROMIC FILM AND A METHOD FOR FABRICATING THE SAME

[75] Inventors: Masaaki Suzuki; Kumiko Moriyama; Eiji Ando, all of Osaka, Japan

[73] Assignee: Matsushita Electric Industrial Co., Ltd., Japan

[21] Appl. No.: 561,632

[22] Filed: Aug. 2, 1990

[30] Foreign Application Priority Data

Aug. 3, 1989 [JP] Japan ................... 1-201589
Mar. 29, 1990 [JP] Japan ................... 2-82437

[51] Int. Cl.$^5$ .................................. G03C 1/72
[52] U.S. Cl. .................. 430/345; 428/17; 428/341; 428/343; 428/962
[58] Field of Search ........... 430/345.17, 341, 343, 430/270, 962

[56] References Cited

U.S. PATENT DOCUMENTS

3,320,067  5/1967  Taylor .
3,501,410  3/1970  Newland et al. .
4,741,920  5/1988  Ueno et al. .
4,913,948  4/1990  Ando et al. .................. 430/495

FOREIGN PATENT DOCUMENTS

078464  12/1974  Japan .

OTHER PUBLICATIONS

Thin Solid Films, vol. 132, 1985, pp. 243–248, Lausanne, CH; M. Shimomura et al.: "Preparation of Langmuir-Blodgett films of azobenzene amphiphiles as polyion complexes".
J. Photopolym. Sci. Technol., vol. 2, No. 2, 1989, pp. 147–152; T. Seki et al.: "Photochromism of spiropyrans in bilayers intercalated between a smectitic clay".
Thin Solid Films, vol. 178, 1989, pp. 103–108, Lausanne, CH; E. Ando et al.: "Molecular arrangements of photochromic spiropyrans on a subphase".

Primary Examiner—Charles L. Bowers, Jr.
Assistant Examiner—Thorl Chea
Attorney, Agent, or Firm—Lowe, Price, LeBlanc & Becker

[57] ABSTRACT

A photochromic material having a thin film of an ion complex of a photochromic substance having an anionic group and a cationic surface active agent is described. Since the surface active agent is used, a uniform film with good photochromism can be obtained. A method for fabricating the photochromic material is also described.

31 Claims, 3 Drawing Sheets

PHOTOCHROMIC MATERIALS HAVING A THIN PHOTOCHROMIC FILM AND A METHOD FOR FABRICATING THE SAME

BACKGROUND OF THE INVENTION

1. Field of the Invention

This invention relates to photochromic materials having a thin photochromic film and also to a method for fabricating the photochromic material.

2. Description of the Prior Art

Photochromic materials are known as substances which undergo reversible color changes by irradiation of light. A number of organic photochromic substances are known as undergoing photoreactions such as cis-trans isomerization, photo-ring-cleavage reactions, photodimerization and the like.

These photochromic materials or substances have wide utility in the fields of glasses whose color is changed by exposure to UV rays, photo-switching devices wherein changes in the refractive index or absorption of light are utilized, or erasable optical memories, and the like. Photochromic substances have been frequently employed in the form of a thin film formed on a support. For the formation of the thin film, many techniques have been developed and used, including casting techniques, dispersion-in-polymer casting techniques wherein the substances are dispersed in polymers, vacuum deposition techniques, the Langmuir-Blodgett technique (hereinafter referred to simply as LB technique or method), and the like.

When the casting, dispersion-in-polymer casting and vacuum deposition techniques are used to make a thin film from photochromic substances which exhibit a good photochromic reaction in a solution, a stable photochromic reaction may not occur in the thin film. The reasons for this are considered as follows: (1) the photochromic substance is crystallized in the thin film; (2) the photochromic substance is in such an associated state that is unlikely to undergo the photochromic reaction; and (3) the photochromic substance is not dispersed uniformly, so that a homogeneous film is not obtained. The LB method is advantageous over the above techniques in that since a monomolecular film of a good quality is formed at the interface between the gas and the liquid, the above problems are not likely to be raised. However, limitation is placed on the LB method. More particularly, in order to form a monomolecular film at the interface, the photochromic substance should have surface activity and a long-alkyl chain. This means that both photochromic substances having no long-chain hydrocarbon group and water-soluble photochromic substances cannot be applied by the LB method.

SUMMARY OF THE INVENTION

It is an object of the invention to provide a photochromic material which comprises a thin film of photochromic substances having an anionic group used in combination with cationic surface active substances whereby good photochromism is exhibited irrespective of the thickness of the thin film and the film is homogeneous and has a good quality.

It is another object of the invention to provide a method for fabricating a photochromic thin film which is uniform in film quality and which exhibits good photochromism.

According to one embodiment of the invention, there is provided a photochromic material which comprises a support and a photochromic thin film formed on the support, the photochromic thin film being made of an ion complex of an anionic photochromic substance having an anionic group and a cationic surface active agent. The thin film may be either a monomolecular film or a built-up film.

According to another embodiment of the invention, there is provided a method for fabricating a photochromic material which comprises the steps of mixing an organic photochromic substance having an anionic group and a cationic surface active agent in a solvent until an ion complex is formed, applying the mixture onto a support, and drying the applied mixture to form a thin film of the ion complex capable of undergoing photochromism on the support. The thin film used herein should preferably have a thickness of from 20 angstroms to 10 micrometers, within which the ion complex can satisfactorily exhibit the photochromism. Because the cationic surface active agent has the capability of forming a self-constructing molecular assembly structure, the thin film obtained becomes homogeneous and high in quality. Moreover, the ion complex has a high degree of freedom of movement of the molecule. As a result, the structural change caused by the photoreaction is easier to occur, thus leading to better photochromism.

According to a further embodiment of the invention, there is also provided a method for fabricating a photochromic material having a photochromic thin film which comprises the steps of dispersing a cationic surface active agent having at least one linear hydrocarbon group having from 8 to 30 carbon atoms in water until said cationic surface active agent is molecularly assembled, adding an aqueous solution of a photochromic substance having an anionic group to the aqueous dispersion to form an ion complex on a surface of the molecularly assembled cationic surface active agent, applying the resulting mixture onto a support, and drying the applied mixture to from a thin film of the ion complex. In this embodiment, the cationic surface active agent is initially formed into a molecular assembly structure by dispersion in water under agitation such as by ultrasonic waves. Some amines or quaternary ammonium compounds having a long-chain hydrocarbon group are capable of forming such a molecular assembly structure, particularly, a bimolecular film structure wherein the hydrophobic long-chain hydrocarbon groups of the respective molecules of the compound are facing each other so that hydrophilic groups are arranged outwardly in the structure.

DETAILED DESCRIPTION AND EMBODIMENTS OF THE INVENTION

Figure 1:
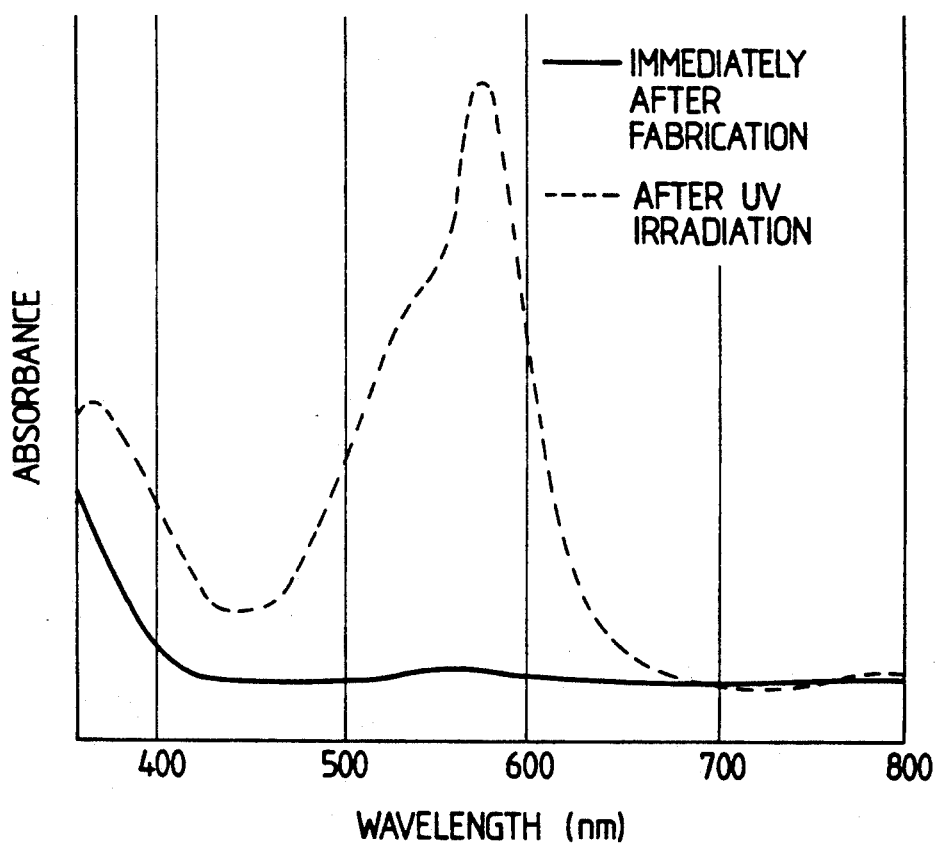
FIG. 1 is an absorption spectrum chart of a photochromic thin film obtained in Example 1 according to the invention.

The photochromic material according to the invention comprises a support on which a photochromic thin film made of an ion complex of an organic photochromic substance having an anionic group and a cationic surface active agent is formed.

The support may be made of transparent materials such as glass, quartz, synthetic resins and the like, and other materials such as metals, semiconductors and the like. The shape of the support may depend on the use and includes, for example, a disk, a sheet, a plate, a rod, a fiber or the like.

The photochromic film formed on the support has a thickness of from 20 angstroms to 10 micrometers although depending on the types of photochromic substance and surface active agent, the type and use of photochromic material and the like.

The organic photochromic substances should have an anionic group which is essentially required for forming ion complexes with cationic surface active agents. Examples of the anionic group include a sulfo group, a carboxyl group, a thiocarboxyl group, a fulfoamino group, a phosphoric ester group, a phosphonic group and the like. The type of organic photochromic substance is not critical provided that it exhibits photochromism and has an anionic group capable of forming ion complexes with cationic surface active agents.

Preferably examples of the organic photochromic substances include spiropyran compounds which are soluble in water and have never been used for forming a thin film according to the LB technique using a water medium. Examples of the spiropyran compounds are those compounds of the following formulae

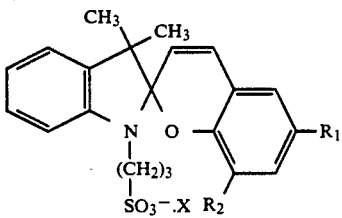

wherein X represents H+ or HN+(C₂H₅)₃, R₁ represents NO₂, and R₂ represents H or OCH₃,

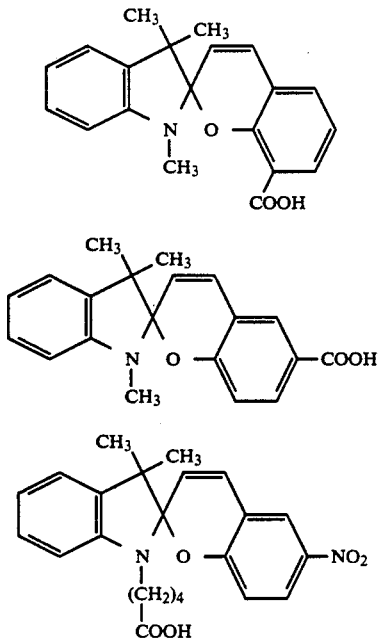

These spiropyran compounds have no long-chain hydrocarbon group and a sulfo or carboxyl group, so that they are soluble in water. The water-soluble spiropyran compounds have never been formed as a thin film according to the LB method. Moreover, if these compounds are applied singly by casting, dispersion-in-polymer casting or vacuum deposition, it is difficult to obtain a film of good quality or a film which exhibits good photochromism. As a matter of course, the photochromic compounds having an anionic group are not limited to those stated above, but any photochromic compounds having an anionic group may be used in the practice of the invention provided that they are able to form ion complexes with cationic surface active agents.

The cationic surface active agents useful in the present invention include primary, secondary and tertiary amines and quaternary ammonium compounds which have at least one hydrocarbon group having from 8 to 30 carbon atoms. Aside from the amine and ammonium compounds mentioned above, long-chain surface active agents having a pyridinium group or an imidazole group may be used. Specific examples of the cationic surface active agents include a diotadecyldimethylammonium compound, an octadecylamine compound, a hexadecyldimethylamine compound, a tridodecylmethylammonium compound, a N-docosylpyridinium compound, a N-dodecylimidazole compounds, a N,N'-dioctadecylviologen compound, a phosphatidyl choline compound and the like.

Of these, the primary, second and tertiary amines and quaternary ammonium compounds are preferred. More specifically, the dioctadecyldimethylammonium compound which is capable of forming a bimolecular film which is in a self-constructing molecular assembly structure as set forth before is more preferred because a homogeneous thin film is more likely to be formed.

The fabrication of the thin film made of ion complexes of photochromic substances having an anionic group and cationic surface active agents is described.

In an initial step, the ion complex is prepared. The preparation may be made by mixing two ingredients in a solvent therefor, or the ion complex may be formed by first providing an aqueous solution of a water-soluble photochromic compound having an anionic group and then spreading a solution of a cationic surface active agent on the aqueous solution of the photochromic compound having an anionic group by which there is obtained a monomolecular film of an ion complex which has been formed at the interface between the aqueous solution and the cationic surface active agent. Alternatively, a cationic surface active agent capable of forming a bimolecular assembly structure may be placed in water and dispersed, for example, by irradiation with supersonic waves to form a bimolecular assembly structure of the agent dispersed in the water. Thereafter, a photochromic substance having an anionic group is added to the dispersion, by which the substance is adsorbed on the surface of the bimolecular assembly structure thereby forming an ion complex.

Any solvent capable of dissolving the two ingredients is usable. Examples of the solvent include alcohols such as methyl alcohol, ethyl alcohol, isopropyl alcohol, phenol and the like, hydrocarbons such as hexane, cyclohexane and the like, halogenated hydrocarbons such as chloroform, dichloroethane, carbon tetrachloride and the like, aromatic hydrocarbons such as benzene, toluene and the like, ethers such as ethyl ether, tetrahydrofuran and the like, and ketones such as acetone, ethyl methyl ketone and the like. These solvents may be used singly or in combination. The two ingredients are mixed substantially at equimolar amounts.

In all the cases for the preparation set out above, the concentration of the anionic photochromic compound or the cationic surface active agent may depend on the manner of film formation and is usually in the range of from 1μ mol/liter to 1 mo/liter.

The ion complex is readily formed by mixing or contacting the two ingredients with each other at temperatures of from 5° to 80° C.

The formation of the ion complex can be confirmed by infrarted spectroscopy.

When the ion complex has been once formed in such a way as stated above, a thin film can be formed without any difficulty. For instance, when the two ingredient are mixed in a solvent to form an ion complex, the solution may be applied by spin coating, casting, the LB method or the like. Alternatively, if the ion complex is formed at the interface between two solutions, the LB method is preferably used after spreading one of the solutions on the other solution. When the LB method is used, a number of monomolecular films may be built up by a usual manner and ordinary film-forming conditions including a surface pressure and a build-up speed may be used in the practice of the invention.

These and other applications of the ion complex are particularly described in examples.

The thin film formed on a support may be allowed to stand whereby the solvent or water is removed to obtain a dry thin film.

The present invention is more particularly described by way of examples.

EXAMPLE 1

A spiropyran compound of the following formula (I) having a sulfo group at the N position and a surface active agent of the following formula (II)

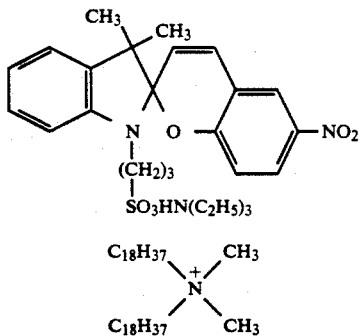

were provided at equimolar amounts and mixed in ethyl alcohol at a concentration of 1 mmols/liter for each ingredient by stirring for 10 minutes by the use of a magnetic stirrer, thereby forming an ion complex of these compounds. The resultant solution was colorless. When the solution was irradiated with a UV ray with a wavelength of 366 nm, it was turned into a colored solution having an absorption maximum in the vicinity of 540 nm, thus exhibiting good photochromism.

The solution was spin coated onto a substrate under conditions of a spinning frequency of 2000 r.p.m. and a spinning time of 20 seconds, thereby forming a photochromic thin film with a thickness of 1000 angstroms. The photochromic characteristic of the thin film obtained above is shown in FIG. 1 wherein the absorption spectrum by solid line are those obtained immediately after the fabrication and the absorption spectrum by broken line are those after UV irradiation.

From the figure, it will be seen that when the UV irradiation is made, the thin film is changed from a colorless state to a colored state with an absorption maximum at a wavelength of 580 nm. Thus, good photochromism is ensured. The X-ray diffraction analysis of the thin film revealed that the film had a bimolecular film structure with a homogeneous film quality.

For comparison, the above procedure was repeated without use of any cationic surface active agent. The resultant solution showed good photochromism when it was irradiated with a UV ray with a wavelength of 366 nm, i.e. the colorless solution was turned into a colored solution having an absorption at about 540 nm. The solution was applied on a substrate by spin coating in the same manner as described above. The resultant film was kept colorless after irradiation with UV rays and did not thus exhibit any photochromism.

EXAMPLE 2

A spiropyran compound of the formula (III) having a sulfo group at the N position and a surface active agent of the formula (II) used in Example 1 were provided at equimolar amounts and mixed in a mixed solvent of methyl alcohol and chloroform in equal amounts, thereby forming an ion complex thereof.

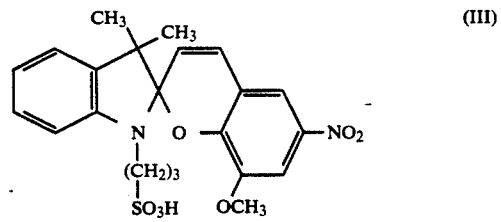

The resultant solution was spread over the gas-liquid interface of a subphase of pure water, obtained by distilling once ion exchanged water, at a temperature of the water of 18° C. A monomolecular film was formed at the gas-liquid interface at a compression speed of 10 mm/minute The spiropyran compound of the formula (III) is soluble in water and cannot form a monomolecular film when used singly. When the ion complex was formed by combination with the cationic surface active agent, the surface activity was imparted, thereby ensuring formation of a stable monomolecular film at the gas-liquid interface.

Figure 2:
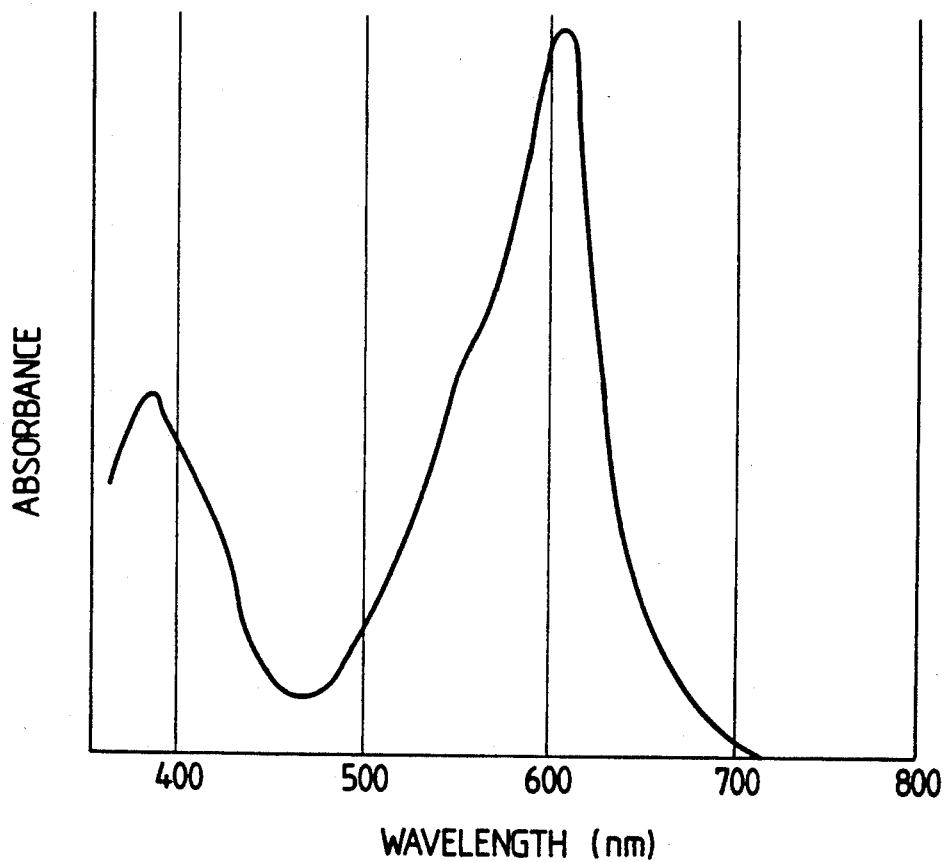
FIG. 2 is an absorption spectrum chart of a photochromic thin film obtained in Example 2.

Five monomolecular films were built up on a quartz substrate under conditions of a surface pressure of 30 mN/m and a build-up speed of 10 mm/minute. The built-up film of the ion complex had an absorption spectrum characteristic shown in FIG. 2. The figure revealed that the built-up film of the ion complex had an absorption maximum in the vicinity of 610 nm.

As will become apparent from this example, when the photochromic substance having originally no surface activity is imparted with surface activity by combination with cationic surface active agents, a monomolecular film of the resultant ion complex containing the photochromic substance can be formed without adversely influencing the photochromism of the photochromic substance. This makes it possible to apply the LB method to photochromic substances to which the LB method has not been applied because of the absence of a long-chain hydrocarbon group and which have an anionic group. Since the LB method can be used, the resultant film becomes uniform in quality.

EXAMPLE 3

An aqueous solution of a spiropyran compound of the formula (III) used in Example 2 at a concentration of 1μ mol/liter was provided as a subphase. Over the gas-liquid interface of the subphase was spread a cationic surface active agent of the formula, $CH_3(CH_2)_{17}NH_2$, which was dissolved in chloroform at a concentration of 1 mmol/liter, thereby forming a monomolecular film. The film was compressed at a rate of 10 mm/minute until the surface pressure reached 30 mN/m, followed by allowing to stand at a constant pressure of 30 mN/m for 30 minutes thereby causing the spiropyran to be adsorbed on the monomolecular film of the surface active agent. Thus, a monomolecular film of the ion complex was formed.

The monomolecular film of the ion complex was formed according to the LB method wherein five built-up films were formed on a quartz substrate at a surface pressure of 30 mN/m and a build-up speed of 10 mm/minute. The LB film of the spiropyran forming the ion complex assumed a deep blue color with an absorption maximum being at about 610 nm. The film quality was good with good photochromism.

EXAMPLE 4

The cationic surface active agent of the formula (II) indicated before was added to distilled water at a concentration of 5 mmols/liter and irradiated with supersonic waves for 10 minutes, thereby dispersing the agent to have a bimolecular film structure in the water. Thereafter, an aqueous solution of the spiropyran compound of the formula (I) indicated before with a concentration of 5 mmols/liter was added to the dispersion and allowed to stand for 30 minutes or over to obtain an ion complex solution wherein the spiropyran compound was adsorbed on the surface of the bimolecular film. The resultant aqueous solution was applied onto a quartz substrate and dried overnight to obtain a transparent, homogeneous cast thin film in a thickness of 5 μm.

Figure 3:
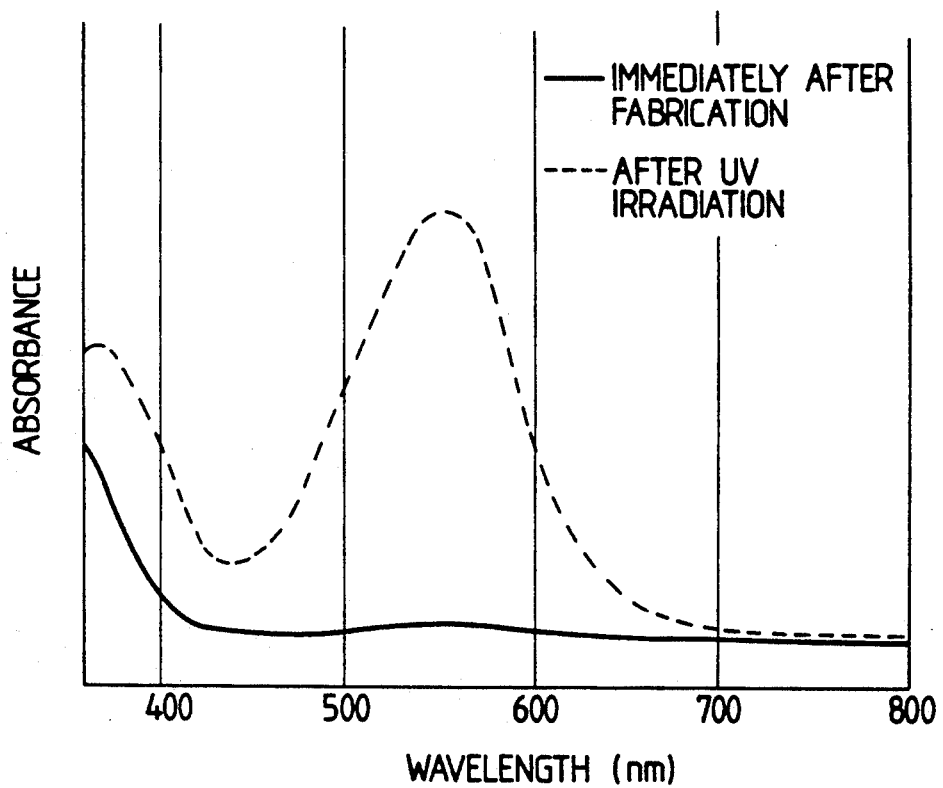
FIG. 3 is an absorption spectrum chart of a photochromic thin film obtained in Example 4.

The X-ray diffraction analysis of the thin film revealed that it had a bimolecular film structure. The thin film was colorless after the formation and was changed to a dark pink color by UV irradiation. In FIG. 3, there is shown an absorption spectrum chart of the thin film wherein the spectrum shown by solid line is that obtained immediately after the formation and the spectrum by broken line is after UV irradiation. This figure revealed that the colored product had an absorption maximum at about 570 nm and the absorption intensity was reduced by irradiation of visible light, thus exhibiting good photochromic characteristics.

EXAMPLE 5

A spiropyran compound of the following formula (IV) and the cationic surface active agent of the formula (II) used in the foregoing examples were mixed in a mixed solvent of methyl alcohol and benzene at equal amounts and allowed to stand for 30 minutes or over to form an ion complex.

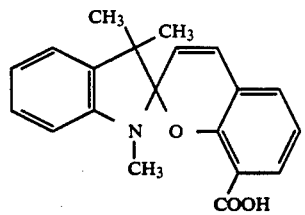

(IV)

The resultant solution was spread over once distilled water to form a monomolecular film. The formation of the monomolecular film at the gas-liquid interface was conducted at a compression speed of 10 mm/minute. The spiropyran (IV) is soluble in water and is not used up to now to form a monomolecular film when used singly. However, the combination with the surface active agent (II) makes it possible to form a monomolecular film by formation of the ion complex.

The monomolecular films was built-up on a quartz substrate on a quartz substrate at a surface pressure of 20 mN/m and a build-up speed of 10 mm/min. The resultant film was uniform in quality and had an absorption maximum of about 420 nm in a colored state. The absorption intensity could be reduced by irradiation of a laser beam with an oscillation wavelength of 420 nm, thus showing good photochromism.

What is claimed is:

1. A photochromic material which comprises a support and a photochromic thin film formed on the support, the photochromic thin film being made of an ion complex of (a) a photochromic water soluble spiropyran compound of having an anionic group and (b) a cationic surface active agent which is a member selected from the group consisting of a primary, secondary, and tertiary amine having from 8 to 30 carbon atoms and quaternary ammonium compound having at least one linear saturated hydrocarbon group having from 8 to 30 carbon atoms.

2. A photochromic material according to claim 1, wherein said thin film is a monomolecular film of the ion complex.

3. A photochromic material according to claim 1, wherein said thin film is a built-up film of monomolecular layers of the ion complex.

4. A photochromic material according to claim 1, wherein said spiropyran compound is of the following general formula

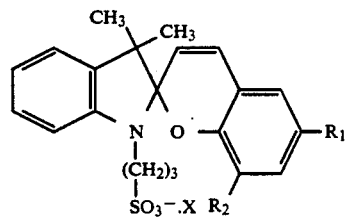

wherein X represents $H^+$ or $HN^+(C_2H_5)_3$, $R_1$ represents $NO_2$, and $R_2$ represents H or $OCH_3$.

5. A photochromic material according to claim 1, wherein said spiropyran compound is of the following formula

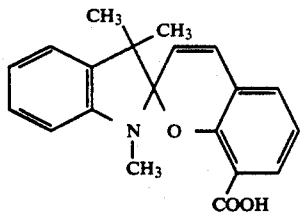

6. A photochromic material according to claim 1, wherein said spiropyran compound is of the following formula

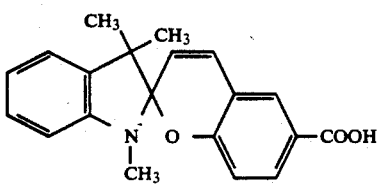

7. A photochromic material according to claim 1, wherein said spiropyran compound is of the following formula

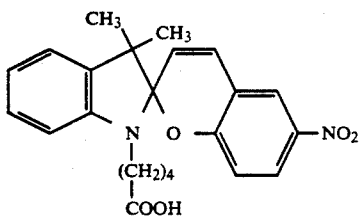

8. A photochromic material according to claim 1, wherein said cationic surface active agent is a primary, secondary or tertiary amine having at least one linear saturated hydrocarbon group having from 8 to 30 carbon atoms.

9. A photochromic material according to claim 8, wherein said cationic surface active agent is of the formula, $CH_3(CH_2)_{17}NH_2$.

10. A photochromic material according to claim 1, wherein said cationic surface active agent is a quaternary ammonium compound having at least one linear saturated hydrocarbon group having from 8 to 30 carbon atoms.

11. A photochromic material according to claim 10, wherein said cationic surface active agent is of the following formula

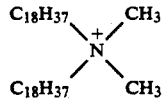

12. A method for fabricating a photochromic material having a photochromic thin film which comprises the steps of providing an ion complex of (a) a photochromic water soluble spiropyran compound of having an anionic group and (b) a cationic surface active agent which is a member selected from the group consisting of a primary, secondary, and tertiary amine having from 8 to 30 carbon atoms and quaternary ammonium compound having at least one linear saturated hydrocarbon group having from 8 to 30 carbon atoms, applying the ion complex onto a support, and drying the applied mixture to form a thin film of the ion complex capable of exhibiting photochromism on the support.

13. The method according to claim 12, wherein said ion complex is provided by mixing the organic photochromic substance having an anionic group and the cationic surface active agent in a solvent and the resulting mixture is applied onto the support.

14. The method according to claim 12, wherein said ion complex is provided by providing a solution of the photochromic substance and spreading a cationic surface active agent at a gas-liquid interface of the solution thereby forming the ion complex at the gas-liquid interface.

15. The method according to claim 12, wherein said spiropyran compound is of the following general formula

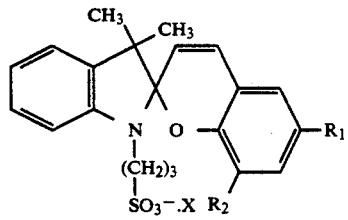

wherein X represents $H^+$ or $HN^+(C_2H_5)_3$, $R_1$ represents $NO_2$, and $R_2$ represents H or $OCH_3$.

16. The method according to claim 12, wherein said spiropyran compound is of the following formula

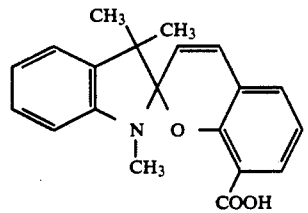

17. The method according to claim 12, wherein said spiropyran compound is of the following formula

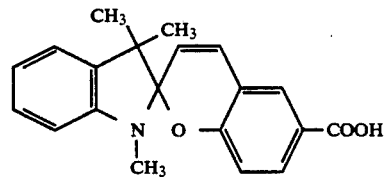

18. The method according to claim 15, wherein said spiropyran compound is of the following formula

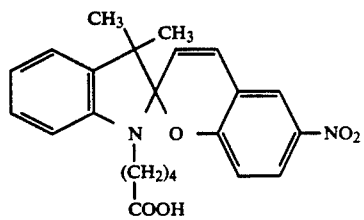

19. The method according to claim 12, wherein said cationic surface active agent is a primary, secondary or tertiary amine having at least one linear saturated hydrocarbon group having from 8 to 30 carbon atoms.

20. The method according to claim 12, wherein said cationic surface active agent is of the formula, $CH_3(CH_2)_{17}NH_2$.

21. The method according to claim 12, wherein said cationic surface active agent is a quaternary ammonium compound having at least one linear saturated hydrocarbon group having from 8 to 30 carbon atoms.

22. The method according to claim 21, wherein said cationic surface active agent is of the following formula

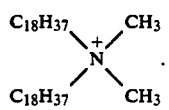

23. A method for fabricating a photochromic material having a photochromic thin film which comprises the steps of dispersing in water a cationic surface active agent which is a member selected from the group consisting of a primary, secondary or tertiary amine having at least one linear saturated hydrocarbon group having from 8 to 30 carbon atoms and a quaternary ammonium compound having at least one linear saturated hydrocarbon group having from 8 to 30 carbon atoms until said cationic surface active agent is molecularly assembled, adding an aqueous solution of a photochromic water soluble spiropyran compound having an anionic group to the aqueous dispersion to form an ion complex on a surface of the molecularly assembled cationic surface active agent, applying the resulting mixture onto a support, and drying the applied mixture to from a thin film of the ion complex.

24. The method according to claim 23, wherein said spiropyran compound is of the following general formula

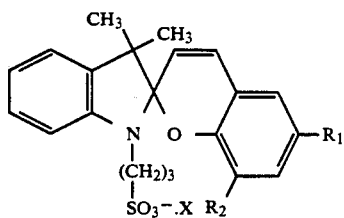

wherein X represents $H^+$ or $HN^+(C_2H_5)_3$, $R_1$ represents $NO_2$, and $R_2$ represents H or $OCH_3$.

25. The method according to claim 23, wherein said spiropyran compound is of the following formula

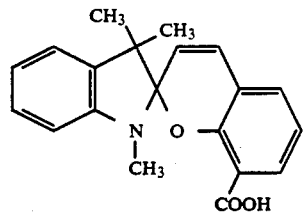

26. The method according to claim 23, wherein said spiropyran compound is of the following formula

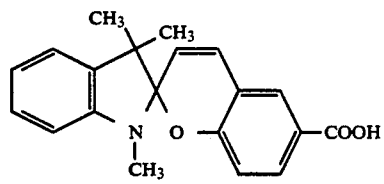

27. The method according to claim 23, wherein said spiropyran compound is of the following formula

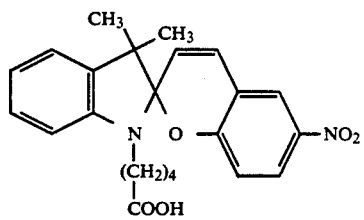

28. The method according to claim 23, wherein said cationic surface active agent is a primary, secondary or tertiary amine having at least one linear saturated hydrocarbon group having from 8 to 30 carbon atoms.

29. The method according to claim 23, wherein said cationic surface active agent is of the formula, $CH_3(CH_2)_{17}NH_2$.

30. The method according to claim 23, wherein said cationic surface active agent is a quaternary ammonium compound having at least one linear saturated hydrocarbon group having from 8 to 30 carbon atoms.

31. The method according to claim 30, wherein said cationic surface active agent is of the following formula

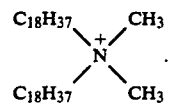

* * * * *